Figure 1:
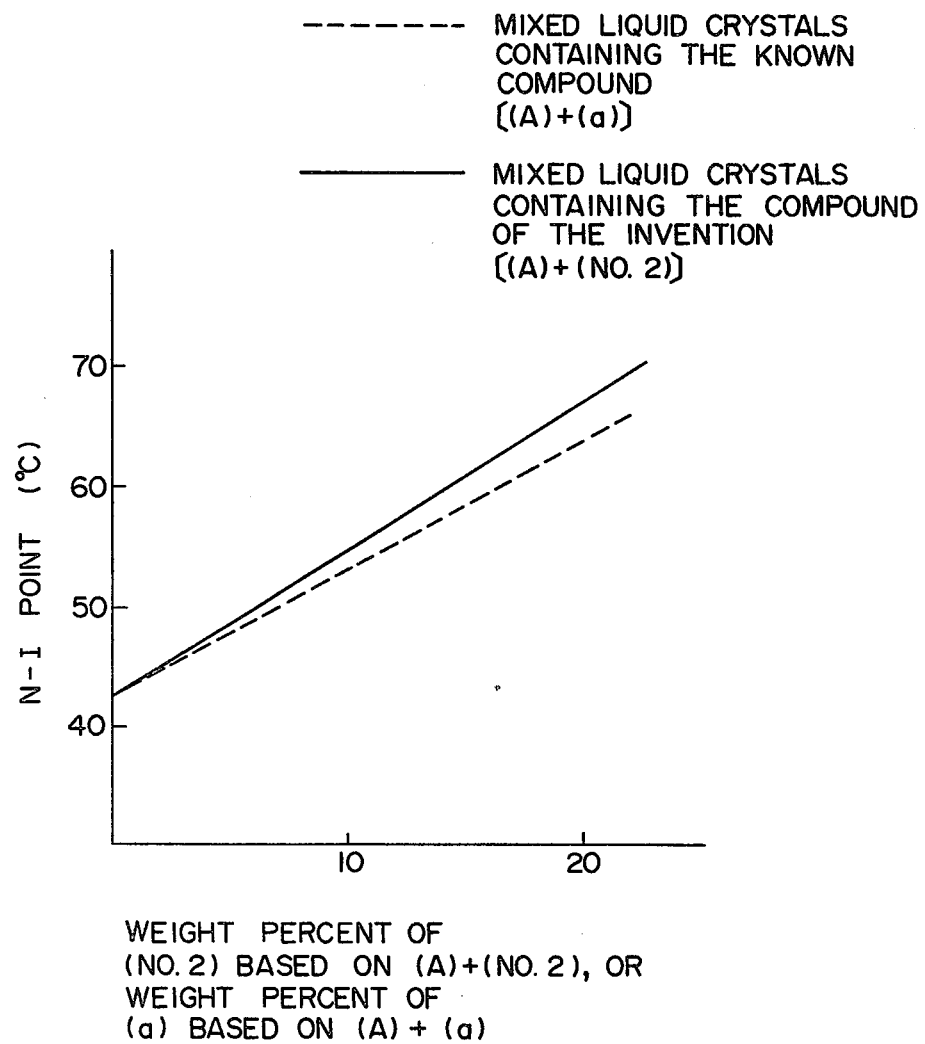

United States Patent [19]

Takatsu et al.

[11] Patent Number: 4,480,117
[45] Date of Patent: Oct. 30, 1984

[54] NEMATIC LIQUID CRYSTALLINE COMPOUNDS

[75] Inventors: Haruyoshi Takatsu, Kodaira; Hisato Sato, Tokyo, both of Japan

[73] Assignee: Dainippin InK and Chemicals, Inc., Tokyo, Japan

[21] Appl. No.: 495,826

[22] Filed: May 18, 1983

[51] Int. Cl.$^3$ .................. C09K 3/34; C07C 69/75; G02F 1/13
[52] U.S. Cl. .................. 560/1; 252/299.5; 252/299.63; 252/299.64; 350/350 R; 350/350 S
[58] Field of Search ............ 252/299.63, 299.64, 252/299.5; 350/350 R, 350 S; 560/1

[56] References Cited

U.S. PATENT DOCUMENTS

| | | | |
|---|---|---|---|
| 4,212,762 | 7/1980 | Dubois et al. | 252/299.64 |
| 4,229,315 | 10/1980 | Krause et al. | 252/299.63 |
| 4,293,434 | 10/1981 | Deutscher et al. | 252/299.63 |
| 4,361,494 | 11/1982 | Osman et al. | 252/299.63 |
| 4,393,258 | 7/1983 | Sato et al. | 252/299.63 |
| 4,400,293 | 8/1983 | Romer et al. | 252/299.63 |
| 4,419,263 | 12/1983 | Praefcke et al. | 252/299.63 |
| 4,439,015 | 3/1984 | Rich et al. | 252/299.63 |

FOREIGN PATENT DOCUMENTS

| | | | |
|---|---|---|---|
| 56501 | 7/1982 | European Pat. Off. | 252/299.63 |
| 58512 | 8/1982 | European Pat. Off. | 252/299.63 |
| 3237367 | 4/1983 | Fed. Rep. of Germany | 252/299.63 |
| 3324774 | 1/1984 | Fed. Rep. of Germany | 252/299.63 |
| 57-48945 | 3/1982 | Japan | 252/299.63 |

Primary Examiner—Teddy S. Gron
Attorney, Agent, or Firm—Sherman & Shalloway

[57] ABSTRACT

A nematic liquid crystalline compound of the general formula

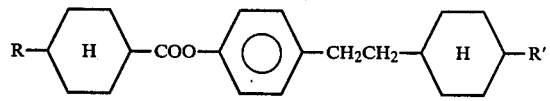

wherein R and R' each represent a linear alkyl group having 1 to 9 carbon atoms, and the two cyclohexane rings are arranged in a trans(equatorial-equatorial) form.

1 Claim, 3 Drawing Figures

NEMATIC LIQUID CRYSTALLINE COMPOUNDS

This invention relates to novel nematic liquid crystalline compounds which are cyclohexanecarboxylic acid derivatives useful as electro-optical display materials.

The novel nematic liquid crystalline compounds provided by this invention are 1-{trans(equatorial-equatorial)-4-alkylcyclohexyl}-2-{trans(equatorial-equatorial)-4-alkylcyclohexanecarbonyloxyphenyl}ethanes represented by the following formula

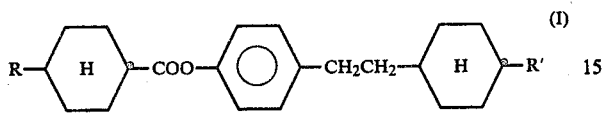

wherein R and R' each represent a linear alkyl group having 1 to 9 carbon atoms, and the two cyclohexane rings are arranged in a trans(equatorial-equatorial) form.

Typical liquid crystal display cells include, for example, a field effect mode cell proposed by M. Schadt et al. [Applied Physics Letters, 18, 127-128 (1971)], a dynamic scattering mode cell proposed by G. H. Heilmeier [Proceedings of the I.E.E.E.,56, 1162-1171 (1968)], and a guest-host mode cell proposed by G. H. Heilmeier [Applied Physics Letters, 13, 91 (1968)] or D. L. White [Journal of Applied Physics, 45, 4718 (1974)].

Liquid crystalline materials used in these liquid crystal display cells are required to have various properties. One important property required commonly of these display cells is that the liquid crystalline materials should have a nematic phase over a broad temperature range including room temperature. Many practical materials having this property are usually prepared by mixing at least one compound having a nematic phase near room temperature with at least one compound having a nematic phase at temperatures higher than room temperature. Many mixed liquid crystals of the above type now in practical use are required to have a nematic phase at least over an entire temperature range of from −30° C. to +65° C. In order to meet this requirement, it is the frequent practice to use compounds having a crystalline-nematic phase transition temperature (C-N point) of about 100° C. and a nematic-isotropic liquid phase transition temperature (N-I) point of about 200° C., such as 4,4'-substituted terphenyl, 4,4'-substituted biphenylcyclohexane and phenyl 4,4'-substituted benzoyloxybenzoate. These compounds, however, have the defect that when they are used in amounts sufficient to adjust the N-I point of the resulting mixed liquid crystals to 65° C. or higher, they increase the viscosity of the mixed liquid crystals, and undesirably reduce their response speeds.

The compounds of formula (I) in accordance with this invention are novel compounds free from this defect. Specifically, when the compounds of formula (I) are mixed with at least one nematic liquid crystalline compound to prepare practical mixed liquid crystals having an N-I point of at least 65° C., they can limit the rise of the viscosity of the mixed liquid crystals to a much smaller extent than the aforesaid known liquid crystalline compounds. Furthermore, since the compounds of formula (I) have very good compatibility with phenyl 4,4'-substituted cyclohexylcarboxylate which is disclosed in Japanese Laid-Open Patent Publication No. 83694/1979 as a nematic liquid crystalline material having excellent characteristics for multiplexing drive, they can be mixed with these known compounds to give better mixed liquid crystals.

The compounds of formula (I) in accordance with this invention can be produced by a process shown schematically below.

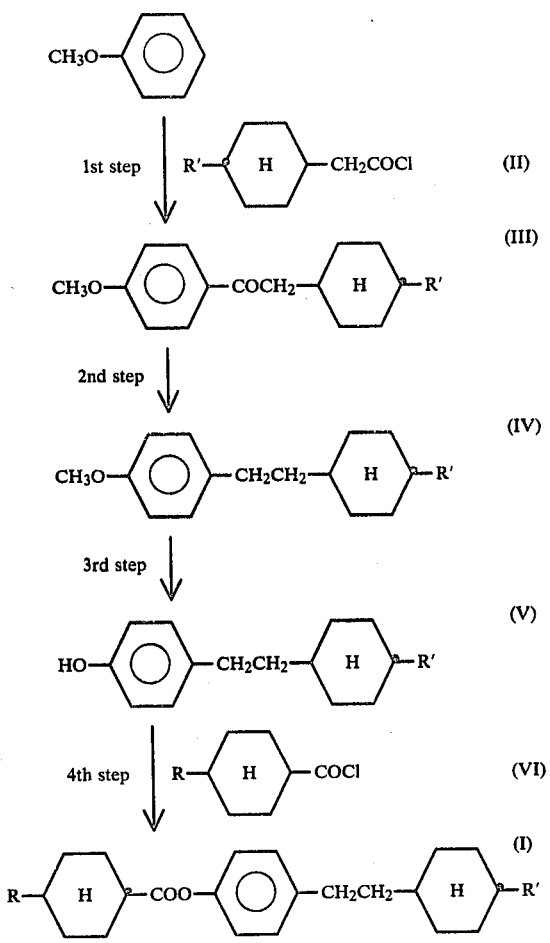

In the first step, the compound of formula (II) and anhydrous aluminum chloride are reacted with anisole in carbon disulfide or nitrobenzene to produce the compound of formula (III).

In the second step, the compound of formula (III) produced in the first step is reacted with hydrazine and potassium hydroxide in ethylene glycol or triethylene glycol to produce the compound of formula (IV).

In the third step, the compound of formula (IV) produced in the second step is reacted with hydrogen bromide or hydrogen iodide in water or acetic acid to produce the compound of formula (V).

In the fourth step, the compound of formula (V) produced in the third step is reacted with the compound of formula (VI) in an inert organic solvent such as ether, benzene or toluene using a basic compound such as pyridine as a catalyst to produce the compound of formula (I) in accordance with this invention.

The transition temperatures of some examples of the compounds of formula (I) so produced are shown in Table 1.

TABLE 1

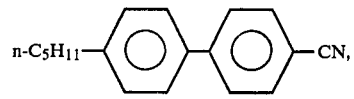

| No. | R | R' | Transition temperature (°C.) |
|---|---|---|---|
| 1 | C$_2$H$_5$— | n-C$_3$H$_7$— | 80(C→N)  145(N⇄I) |
| 2 | n-C$_3$H$_7$— | n-C$_3$H$_7$— | 120(C→N)  163(N⇄I) |
| 3 | n-C$_4$H$_9$— | n-C$_3$H$_7$— | 110(C→N)  160(N⇄I) |
| 4 | n-C$_5$H$_{11}$— | n-C$_3$H$_7$— | 122(C→N)  163(N⇄I) |

In the table, C represents a crystalline phase; N, a nematic phase; and I, an isotropic liquid phase.

The compounds of formula (I) in accordance with this invention are nematic liquid crystalline compounds having weak negative dielectric anisotropy. Hence, they can be used, for example, as materials for dynamic scattering mode cells in the form of mixtures with other nematic liquid crystalline compounds having negative or weakly positive dielectric anisotropy. Or they can be used as materials for field effect mode cells in the form of mixtures with other nematic liquid crystalline compounds having strongly positive dielectric anisotropy.

Typical examples of other nematic liquid crystalline compounds which can preferably be used in admixture with the compounds of formula (I) include phenyl 4,4'-substituted benzoates, phenyl 4,4'-substituted cyclohexanecarboxylates, biphenyl 4,4'-substituted cyclohexanecarboxylates, 4'-substituted phenyl 4(4-substituted cyclohexane carbonyloxy)-benzoates, 4'-substituted phenyl 4(4-substituted cyclohexyl)-benzoates, cyclohexyl 4(4-substituted cyclohexyl)-benzoates, 4,4'-biphenyl, 4,4'-phenylcyclohexane, 4,4'-substituted terphenyl, 4,4'-biphenylcyclohexane, and 2(4'-substituted phenyl)5-substituted pyrimidine.

Table 2 below summarizes the N-I points and viscosities of various mixed liquid crystals composed of 80% by weight of matrix liquid crystals (A) now in widespread use as a nematic liquid crystalline material having excellent characteristics for time multiplex drive and 20% by weight of compounds Nos. 1 to 4 of formula (I) respectively shown in Table 1. Table 2 also gives the N-I point and viscosity of the matrix liquid crystals (A) for comparison.

The matrix liquid crystals (A) is composed of 40 mole% of

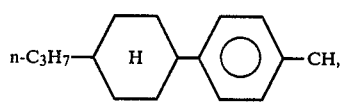

30 mole% of

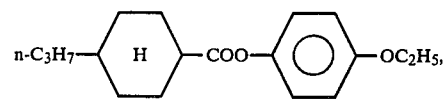

15 mole% of

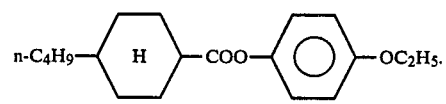

and 15 mole % of

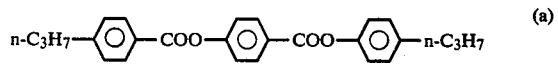

TABLE 2

|  | N—I point (°C.) | Viscosity (centipoises/20° C.) |
|---|---|---|
| (A) | 42.5 | 21.2 |
| (A) + (No. 1) | 62.9 | 23.5 |
| (A) + (No. 2) | 67.2 | 23.5 |
| (A) + (No. 3) | 65.9 | 23.8 |
| (A) + (No. 4) | 67.3 | 24.0 |

It will be seen from the data given in Table 2 that the compounds of formula (I) can increase the N-I points of mixed liquid crystals to a practically sufficient extent without greatly increasing the viscosities of the mixed liquid crystals. The viscosity value of about 24 centipoises/20° C. is considerably lower than the viscosities of various mixed liquid crystals which have an N-I point of at least 65° C. and are now on an average practical level. The high utilitarian value of the compounds of formula (I) is that they can give mixed liquid crystals having such low viscosities.

The effect or advantage of this invention is also demonstrated by the following comparative experiment.

COMPARATIVE EXPERIMENT

A known compound of the following formula

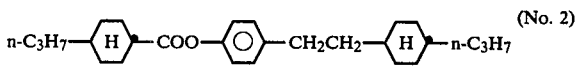
(a)

which has a chemical structure similar to the compound of formula (I) in accordance with this invention and is widely used in order to increase the N-I point of mixed liquid crystals was mixed in various proportions with the matrix liquid crystals (A) described above.

Likewise, one compound of the invention represented by the following formula (No. 2)

n-C$_3$H$_7$—⟨H⟩—COO—⟨O⟩—CH$_2$CH$_2$—⟨H⟩—n-C$_3$H$_7$ was mixed in various proportions with the matrix liquid crystals (A).

The N-I points and viscosities of the two types of mixed liquid crystals so prepared were measured.

Figure 2:
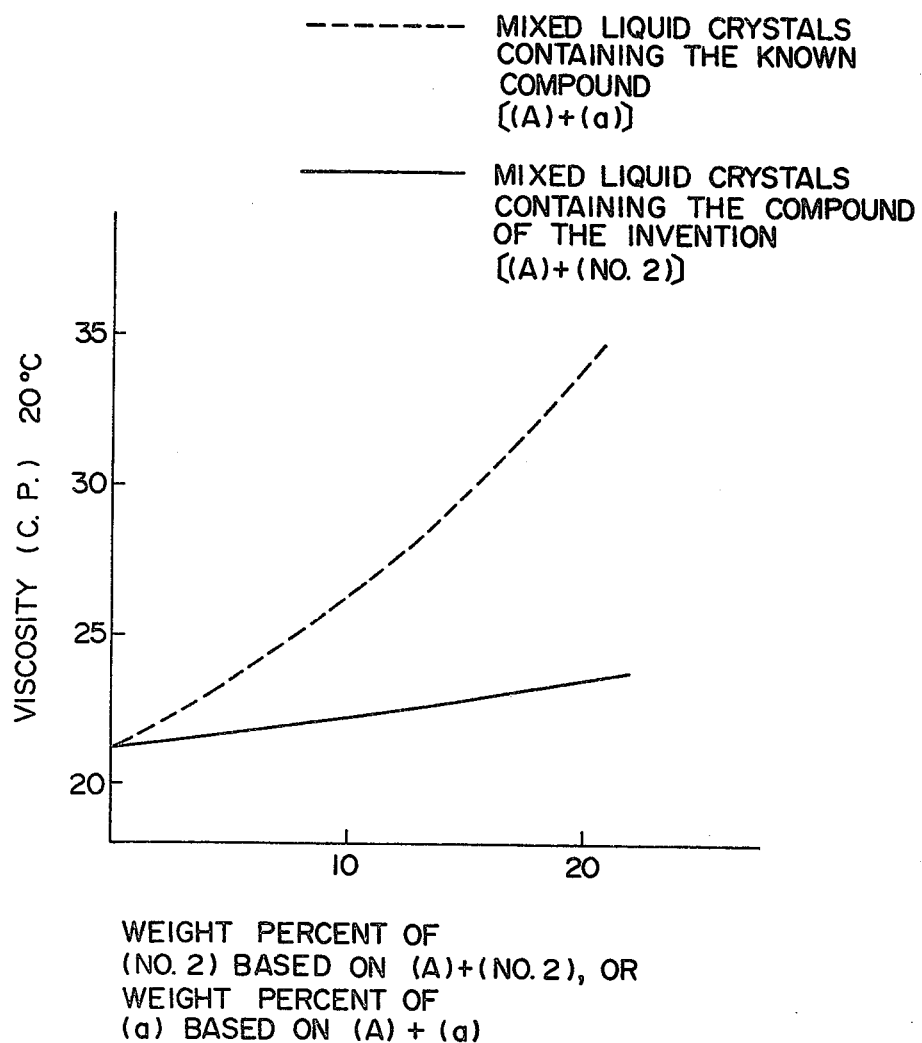
Figure 3:
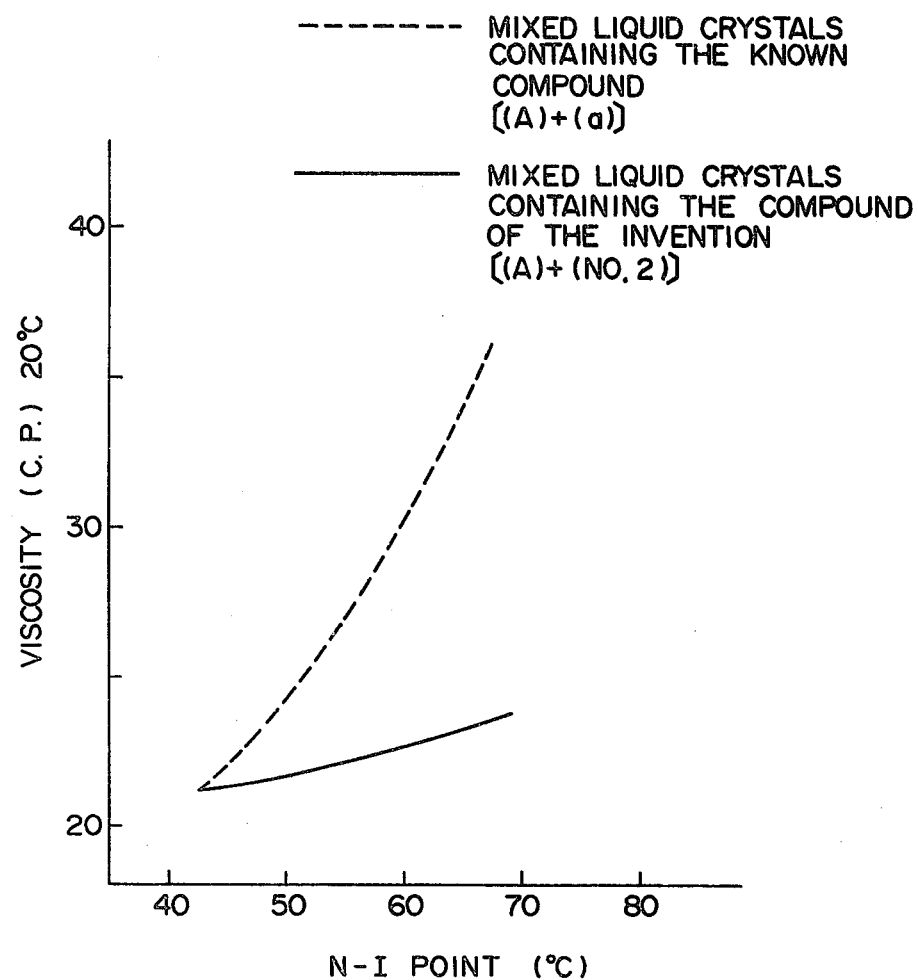

The accompanying drawings are graphs obtained by plotting these measured data. FIG. 1 shows the relation between the N-I point and the amount added. FIG. 2 shows the relation between the viscosity and the amount added. FIG. 3 shows the relation between the N-I point and the viscosity.

The facts given in these graphs demonstrate that the compound of formula (I) in accordance with this invention causes a much smaller increase in viscosity with a rise in N-I point that the typical known compound having a similar structure.

The following non-limitative Examples specifically illustrate the production of the compounds of formula (I) in accordance with this invention.

EXAMPLE 1

Anhydrous aluminum chloride (16.0 g; 0.120 mole) was added to 100 ml of carbon disulfide, and with stirring at room temperature, 20.3 g (0.100 mole) of trans-4-n-propylcyclohexylacetyl chloride was added dropwise. The mixture was stirred further at room temperature, and 10.8 g (0.100 mole) of anisole was added dropwise. The mixture was reacted at 30° to 35° C. for 5 hours. After evaporating carbon disulfide, the reaction mixture was poured into ice water, and the mixture was stirred at 60° C. for 1 hour. After cooling, reaction product was extracted with ether. The extract was washed with water and dried, and the ether was evaporated. The residue was recrystallized from ethanol to give 19.8 g (0.0722 mole) of a compound of the following formula.

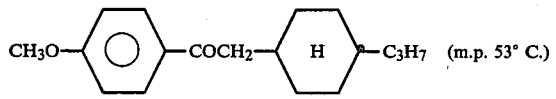 (m.p. 53° C.)

Triethylene glycol (120 ml), 12.6 g (0.202 mole) of 80% hydrazine hydride and 16.3 g (0.247 mole) of 85% potassium hydroxide were added to the resulting compound. The mixture was gradually heated with stirring, and reacted at 160° C. for 5 hours. After cooling, 200 ml of water was added, and the reaction mixture was extracted with benzene. The extract was washed with water, and benzene was evaporated. Then, 150 ml of glacial acetic acid and 27 cc of 47% hydrobromic acid were added to the residue, and the mixture was reacted at the refluxing temperature for 8 hours. After the reaction, the reaction mixture was cooled, and 300 cc of water was added. The mixture was then extracted with ether. The extract was washed with water, and dried over anhydrous sodium sulfate. The ether was evaporated, and the residue was recrystallized from n-hexane to give 12.3 g (0.0500 mole) of a compound of the following formula.

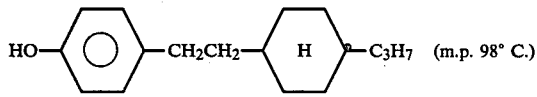 (m.p. 98° C.)

The resulting compound (12.3 g; 0.0500 mole) was dissolved in toluene, and 7.90 g (0.0750 mole) of pyridine was added. With stirring at room temperature, 9.43 g (0.0500 mole) of trans-4-n-ethylcyclohexanecarbonyl chloride was added dropwise. After the addition, the mixture was reacted for 2 hours at the refluxing temperature. The reaction product was extracted with toluene. The extract was washed with water and dried, and toluene was evaporated. The residue was recrystallized from methanol/ethanol to give 15.6 g (0.0407 mole) of a compound of the following formula.

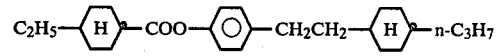

Yield: 40.7%.

Transition temperatures: 80° C. (C→N); 145° C. (N⇌I).

EXAMPLE 2

In the same way as in Exmple 1, a compound of the following formula was produced.

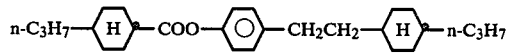

Yield: 43.8%

Transition temperature: 102° C. (C→N); 163° C. (N⇌I).

EXAMPLE 3

In the same way as in Example 1, a compound of the following formula was produced.

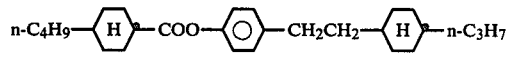

Yield: 41.2%

Transition temperature: 110° C. (C→N); 160° C. (N⇌I).

EXAMPLE 4

In the same way as in Example 1, a compound of the following formula was produced.

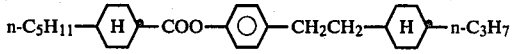

Yield: 43.5%

Transition temperature: 122° C. (C→N); 163° C. (N⇌I).

What is claimed is:

1. A compound of the general formula

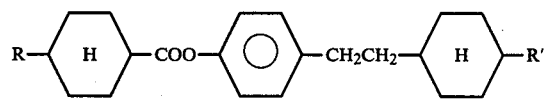

wherein R and R' each represent a linear alkyl group having 1 to 9 carbon atoms, and the two cyclohexane rings are arranged in a trans(equatorial-equatorial) form.

* * * * *

UNITED STATES PATENT AND TRADEMARK OFFICE
CERTIFICATE OF CORRECTION

PATENT NO. : 4,480,117
DATED : October 30, 1984
INVENTOR(S) : Haruyoshi Takatsu; Hisato Sato It is certified that error appears in the above-identified patent and that said Letters Patent is hereby corrected as shown below:

On the title page;

Assignee: delete "Dainippin InK and Chemicals, Inc., and insert -- Dainippon Ink and Chemicals, Inc., --

Signed and Sealed this

Thirtieth Day of July 1985

[SEAL]

Attest:

DONALD J. QUIGG

*Attesting Officer*  *Acting Commissioner of Patents and Trademarks*

UNITED STATES PATENT AND TRADEMARK OFFICE
CERTIFICATE OF CORRECTION

PATENT NO. : 4,480,117
DATED : October 30, 1984
INVENTOR(S) : Haruyoshi Takatsu; Hisato Sato It is certified that error appears in the above-identified patent and that said Letters Patent is hereby corrected as shown below:

On the title page:

Assignee; delete "Dainippin Ink and Chemicals, Inc., and insert
— Dainippon Ink and Chemicals, Inc., —

Priority claimed for — Japanese Application 85032/82
May 21, 1982 —

Signed and Sealed this

Fifteenth Day of July 1986

[SEAL]

Attest:

Attesting Officer

DONALD J. QUIGG

Commissioner of Patents and Trademarks